United States Patent
Latham

(10) Patent No.: US 7,083,585 B2
(45) Date of Patent: Aug. 1, 2006

(54) STRING ARRANGEMENT OF A SEPARATE BACK IMMOBILIZING, DYNAMICALLY SELF-ADJUSTING, CUSTOMIZING BACK SUPPORT FOR A VERTEBRA RELATED PATIENT

(76) Inventor: Mark Alan Latham, 16377 White Blossom Cir., Riverside, CA (US) 92503

(*) Notice: Subject to any disclaimer, the term of this patent is extended or adjusted under 35 U.S.C. 154(b) by 0 days.

(21) Appl. No.: 10/840,597

(22) Filed: May 7, 2004

(65) Prior Publication Data
US 2005/0251074 A1 Nov. 10, 2005

(51) Int. Cl.
*A61F 5/00* (2006.01)

(52) U.S. Cl. .................... 602/19; 602/20

(58) Field of Classification Search ............ 602/5, 602/19–22, 32, 36, 60, 61, 12, 38, 4, 40, 602/71; 128/95.1, 96.1, 102.1–106, DIG. 19; 2/44–45, 92, 311; 24/713.4, 713.5, 714.6, 24/715, 715.1, 715.2
See application file for complete search history.

(56) References Cited

U.S. PATENT DOCUMENTS

| | | | | |
|---|---|---|---|---|
| 4,178,923 A | * | 12/1979 | Curlee ................... | 602/13 |
| 4,475,543 A | * | 10/1984 | Brooks et al. ........... | 602/19 |
| 4,794,916 A | * | 1/1989 | Porterfield et al. ....... | 602/19 |
| 4,976,257 A | * | 12/1990 | Akin et al. .............. | 602/19 |
| 4,991,573 A | * | 2/1991 | Miller ................... | 602/19 |
| 4,993,409 A | * | 2/1991 | Grim ..................... | 602/19 |
| 5,012,798 A | * | 5/1991 | Graf et al. .............. | 602/19 |
| 5,072,725 A | * | 12/1991 | Miller ................... | 602/19 |
| 5,204,993 A | * | 4/1993 | Siemens ................. | 2/461 |
| 5,267,948 A | * | 12/1993 | Elliott .................. | 602/19 |
| 5,310,401 A | * | 5/1994 | Striano ................. | 602/19 |
| 5,362,304 A | * | 11/1994 | Varn ..................... | 602/19 |
| 5,363,863 A | * | 11/1994 | Lelli et al. ............. | 128/876 |
| 5,429,587 A | * | 7/1995 | Gates .................... | 602/19 |
| 5,437,614 A | * | 8/1995 | Grim ..................... | 602/19 |
| 5,437,617 A | * | 8/1995 | Heinz et al. ............. | 602/19 |
| 5,468,216 A | * | 11/1995 | Johnson et al. ........... | 601/24 |
| 5,484,395 A | * | 1/1996 | DeRoche ................. | 602/19 |
| 5,533,961 A | * | 7/1996 | Iwata .................... | 602/19 |
| 5,537,690 A | * | 7/1996 | Johnson .................. | 2/44 |
| 5,551,085 A | * | 9/1996 | Leighton ................ | 2/44 |
| 5,623,728 A | * | 4/1997 | Wagner ................... | 2/462 |
| 5,632,723 A | * | 5/1997 | Grim ..................... | 602/19 |
| 5,651,763 A | * | 7/1997 | Gates .................... | 602/19 |
| 5,688,229 A | * | 11/1997 | Bauer .................... | 602/18 |

(Continued)

*Primary Examiner*—Henry Bennett
*Assistant Examiner*—Shumaya B. Ali
(74) *Attorney, Agent, or Firm*—Eugene Oak

(57) ABSTRACT

A string arrangement for a detachment type waist-protecting belt to hold the vertebra region of a vertebra related patient is provided. The string arrangement enables a separate fastening of the upper portion and lower portion of the belt to form a saddle like shape that fits the contour of the waist of an individual patient dynamically with or without the extra support of a frame. The waist-protecting belt can also be connected to a back supporting frame, which is comprised of two plastic plates, via two guiding nuts, fixed on the center of the exterior side of the inner-half of the rim of each solid plastic plate, guided through the two narrow and long holes found on the wider portions of the belt, and held in place by two wide head bolts which screw on to the nuts. Then the upper portion and lower portion of the frame is adjusted separately by the movement of the upper and lower portion of the belt.

5 Claims, 7 Drawing Sheets

U.S. PATENT DOCUMENTS

| | | | |
|---|---|---|---|
| 5,765,224 A * | 6/1998 | Johnson | 2/44 |
| 5,776,087 A * | 7/1998 | Nelson et al. | 602/19 |
| 5,785,671 A * | 7/1998 | Striano | 602/19 |
| 5,833,638 A * | 11/1998 | Nelson | 602/19 |
| 5,911,697 A * | 6/1999 | Biedermann et al. | 602/19 |
| 5,915,543 A * | 6/1999 | Julin | 2/467 |
| 5,967,998 A * | 10/1999 | Modglin | 602/19 |
| 5,984,885 A * | 11/1999 | Gaylord et al. | 602/19 |
| 6,067,665 A * | 5/2000 | DePalma et al. | 2/468 |
| 6,080,121 A * | 6/2000 | Madow et al. | 602/5 |
| 6,102,879 A * | 8/2000 | Christensen et al. | 602/19 |
| 6,137,675 A * | 10/2000 | Perkins | 361/679 |
| 6,213,968 B1 * | 4/2001 | Heinz et al. | 602/19 |
| 6,267,741 B1 * | 7/2001 | Lerman | 602/18 |
| 6,322,529 B1 | 11/2001 | Chung | |
| 6,336,908 B1 * | 1/2002 | Slautterback | 602/19 |
| 6,419,652 B1 * | 7/2002 | Slautterback | 602/19 |
| 6,517,502 B1 * | 2/2003 | Heyman et al. | 602/5 |
| 6,666,838 B1 * | 12/2003 | Modglin et al. | 602/19 |
| 6,676,620 B1 * | 1/2004 | Schwenn et al. | 602/12 |
| 6,746,413 B1 * | 6/2004 | Reinecke et al. | 602/19 |
| 6,749,579 B1 * | 6/2004 | Schroder | 602/36 |
| D492,787 S * | 7/2004 | Weaver et al. | D24/190 |
| 6,776,767 B1 * | 8/2004 | Reinecke et al. | 602/19 |
| 2001/0020144 A1 * | 9/2001 | Heinz et al. | 602/19 |
| 2002/0068890 A1 * | 6/2002 | Schwenn et al. | 602/19 |

* cited by examiner

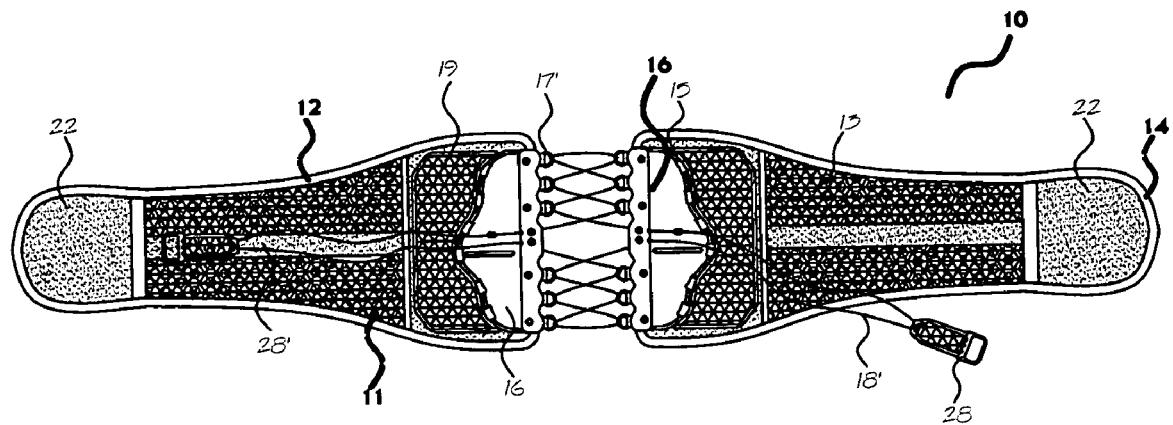
Fig.1 Priority Art
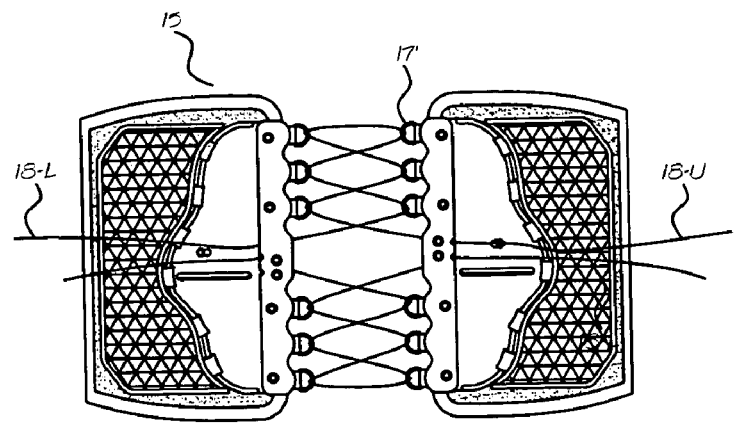
Fig.1-a Priority Art

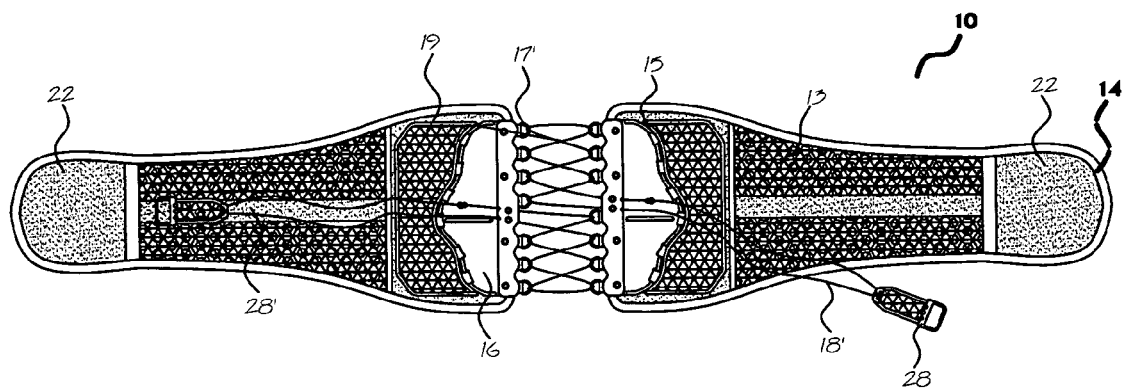
Fig.2
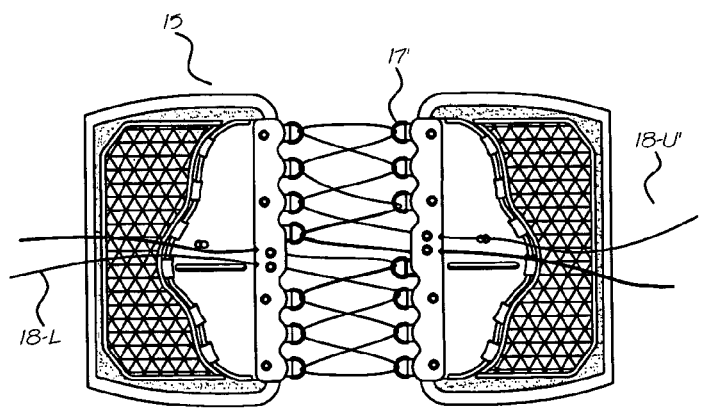
Fig.2-a

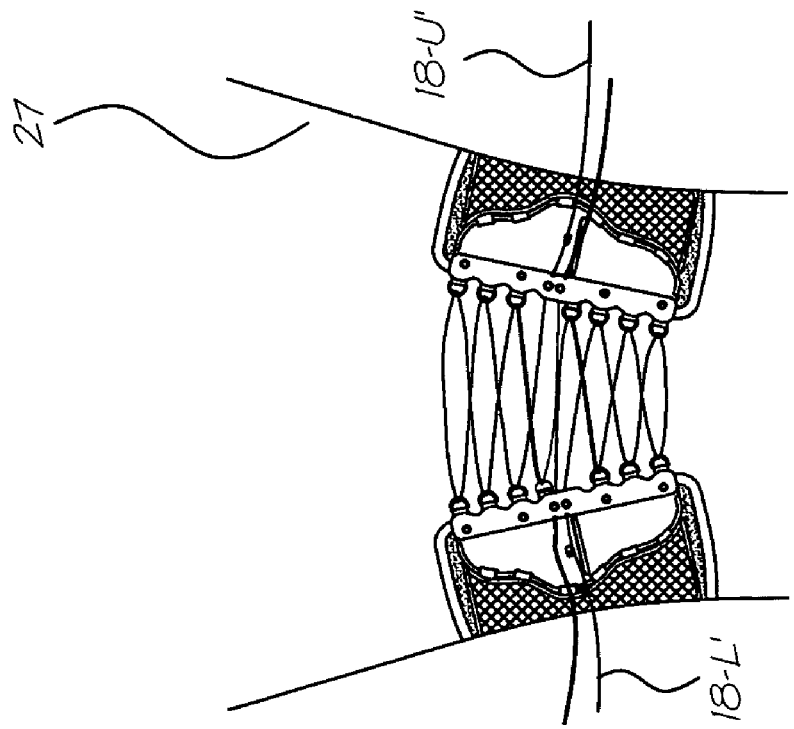
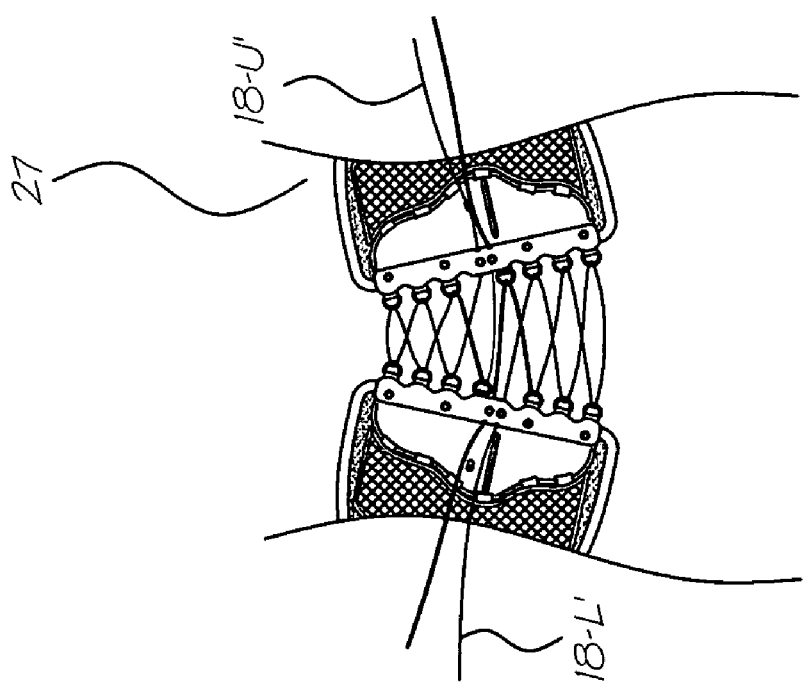

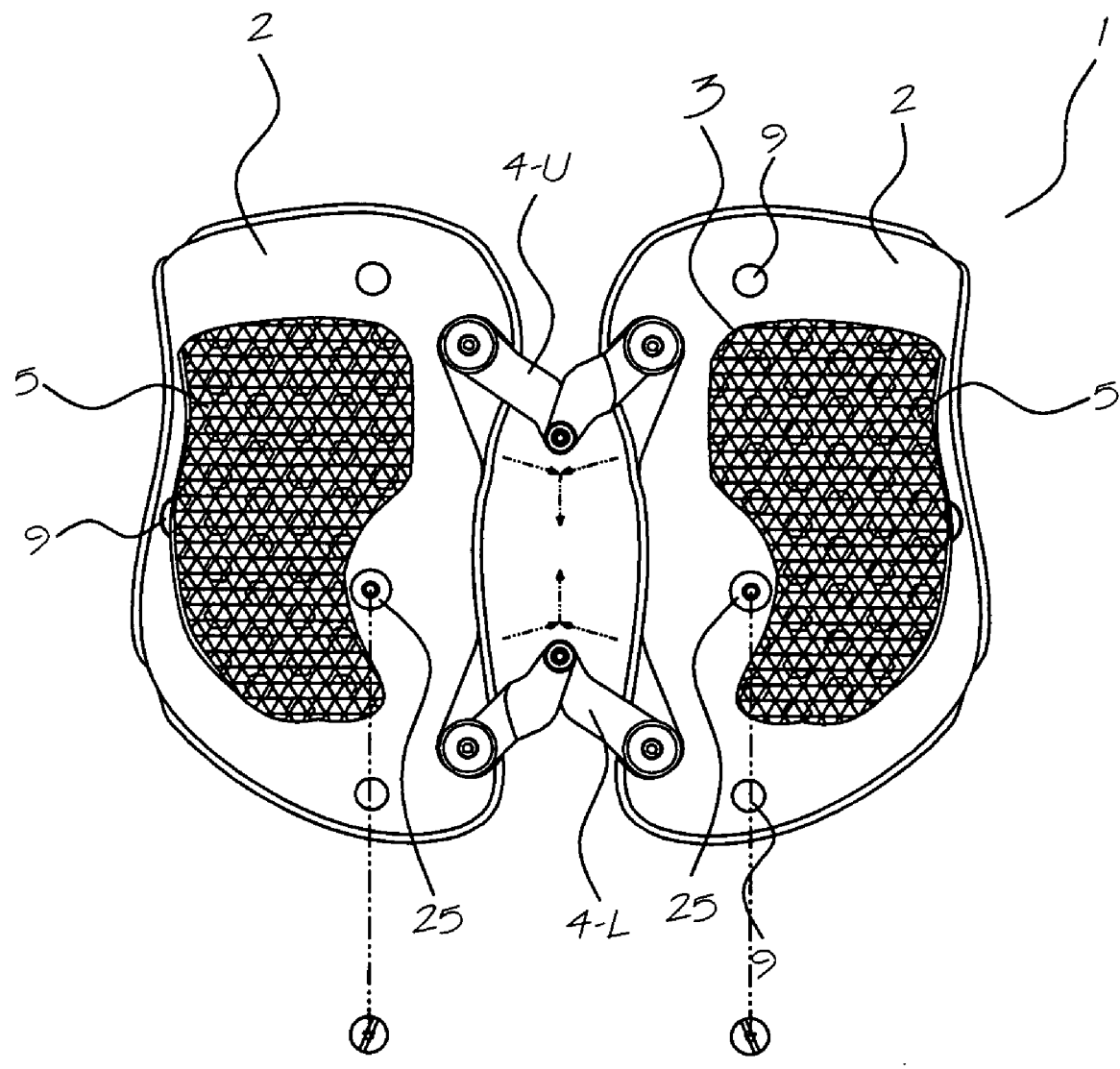
Fig. 4-a

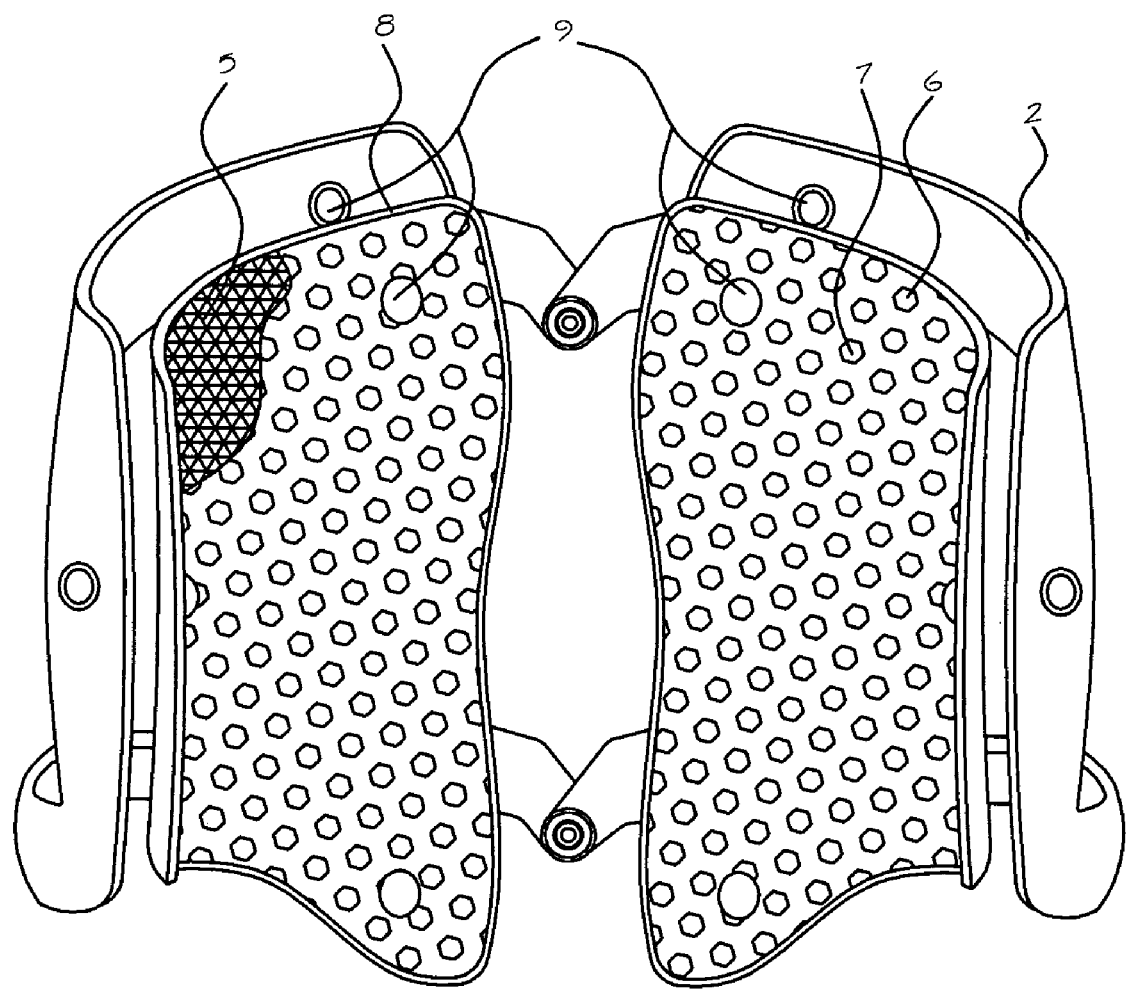
Fig.4-b

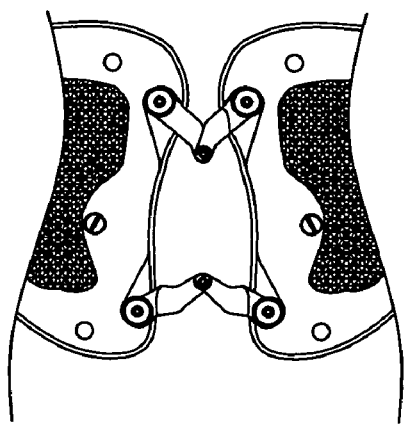
Fig.6-a
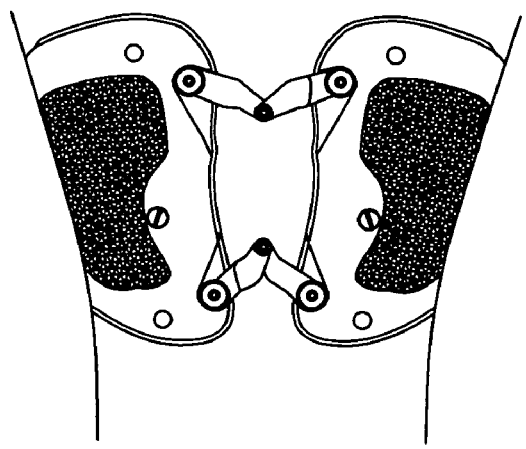
Fig.6-b

STRING ARRANGEMENT OF A SEPARATE BACK IMMOBILIZING, DYNAMICALLY SELF-ADJUSTING, CUSTOMIZING BACK SUPPORT FOR A VERTEBRA RELATED PATIENT

FIELD OF THE INVENTION

The present invention relates to a method of arranging strings on a detachment type waist-protecting belt to hold the vertebra region of a vertebra related patient and permit separate superior and inferior adjustment of the rib and diaphragm area from the hip region of the belt.

BACKGROUND OF THE INVENTION

As is well known in the industry, the waist-protecting belt, known as an abdominal support or a pelvic girdle, is comprised of a resilient belt made of a proper material such as spandex. The role of a waist-protecting belt is to slightly compress and support the waist of a vertebra related patient's body. This prevents pain by keeping the waist in straight vertical alignment. In a recent development of U.S. patent application Ser. No. 10/810,860, I and my colleagues provided an adjustable back frame, which is comprised of two plastic plates, which are connected by two hinges, which are attached to the upper and the lower parts of the plastic plates, to form a saddle like shape that fits the contour of the back of an individual patient dynamically. However, the conventional arrangement of tightening strings fastens the upper and lower part of the frame at the same time.

An improvement is introduced by changing the arrangement of the strings. This new arrangement enables separate compressing of the upper and lower part of the belt to make the back supporting belt more effectively fit the curvature of the patient's body.

DESCRIPTION OF THE PRIOR ARTS

U.S. Pat. No. 6,322,529 to Chung illustrates a detachment type waist-protecting belt including a waist support, which fits a contour of the waist of the human body. The string (107) is aligned in a symmetrical mirror image. FIG. 2 of '529 shows five connecting rings (105) developed at the upper part of each connecting plate (105) and the same number of connecting rings (107) developed at the lower part of each connecting plate (105). FIG. 4 of the same invention shows four connecting rings (105) developed on the upper and lower part of each connecting plate (207). Both ends of the pulling cords (107) respectively pass zigzag from the upper and lower ends of the connecting plates (207) through the connecting rings (110) which are rotatably fastened to the connecting plates (207) by the pins in such a way as to be spaced one from one other in the longitudinal direction by the predetermined distance. As both ends of the pulling cords (107) are pulled left ward and right ward of the connecting plates, the distance between the connecting plates (207) can be shortened, and thereby, the entire waist protecting belt can be tightened at a rear part thereof with equal compression. It does not enable a separate fastening of the upper portion and lower part of the belt to form a saddle like shape that fits the contour of the waist of an individual patient dynamically and permits separate inferior and superior pressure to be applied to the rib and upper stomach and the pelvis region of the patient. None of FIGS. 1–4 of the '529 shows the mechanism of fastening the upper and lower part of the belt separately. The belt of '529 fastens the upper and lower part of the belt with equivalent pressure.

U.S. Pat. No. 5,399,150 Saunders illustrates a lumbosacral back support band provided with a releasable attaching back support system, which is made of one piece of composite band. It does not have any means for adjusting the tightness of the upper and lower part of the composite band.

U.S. Pat. No. 6,213,968B1 to Heinz et al. teaches the material for brace body (12). That brace body (12) is developed along the perimeters of the back brace (10). Referring to the specification of col. 4 lines 66–67 and col. 5 lines 1–17 and FIGS. 1 and 2 of the '968 clearly shows that the brace body (12) is a brim part. Heinz et al. used nylon mesh for the brims of the brace (10), not for the brace body segment (12a) and (12b) that are equivalent to the part of the current application where plastic mesh materials are used. The purpose of using canvass, nylon, polyethylene, nylon mesh or other similar material is to obtain proper ties of rigidity and breathability, in other words, flexibility to allow the wearer breath in and out. No function of releasing sweat and heat from the wearer's body is possible.

U.S. Pat. No. 5,195,948 to Hill, et al. illustrates a back support device comprised of a belt structure designed to fit substantially around the waist of a user. An inflatable air bladder is attached inside the belt structure so that it is positioned adjacent to the lower back when the back support device is worn. The air bladder (40) presses the back of the wearer. The pressure can be adjusted horizontally along the waist of the wearer but cannot be adjusted along the vertical direction of the wearer.

U.S. Pat. No. 5,127,897 to Roller illustrates a therapeutic back support device including a plastic back support plate, which is coupled to a human body to forwardly direct the plate. By adjusting the upper belt (40) and lower belt (30), the wearer can control the contour of the support plate (20).

U.S. Pat. No. 3,889,664 to Heuser, et al. illustrates two torso belt members, joined together with a jack screw connector, intended to apply traction to the user between the pair of belts. Adjustment of the shape of the apparatus consists of extremely complex steps of operating knobs and screws.

None of the prior arts introduces a method of arranging strings on a detachment type waist-protecting belt for a separate adjustment of the belt with two straps.

SUMMARY OF THE INVENTION

A string arrangement for a detachment type waist-protecting belt to hold the vertebra region of a vertebra related patient is provided. The string arrangement enables a separate fastening of the upper portion and lower portion of the belt. The belt is comprised of two elastic bands of identical size, which are equipped with connector plates, eyelids, Velcro® s, and strings. One set of string passes through the eyelids attached at the upper part of both elastic bands. The other set of string passes through the eyelids attached at the lower part of both elastic bands. Each set of strings fastens a different part of the waist protecting belt. The string arrangement of the current invention is applicable to conventional waist protecting belts with the addition of the frame as far as the back supporting frame (plate) is made of a flexible plastic plate or the frame is comprised of separate plates. When wearing a back supporting frame of the above described, equipped with a string arrangement of the current invention, patients, with significant superior and inferior variation between the circumferance of the rib/diaphragm region and the hip/abdomen region, such as, a relatively small rib cage and diaphragm with relatively large hips and abdomen or a relatively large chest and diaphragm with relatively narrow hips and abdomen, will be able to adjust the compression appropriately and achieve more appropriate compression in the different areas than patients accustomed to other fastening string arrangement by being able to adjust the separate areas of the supporting belt independently with mechanical advantage, by themselves.

The waist-protecting belt can be connected to a back supporting frame, which is comprised of two plastic plates, via two guiding nuts, fixed on the center of the exterior side of the inner-half of the rim of each solid plastic plate, guided through the two narrow and long holes found on the wider portions of the belt, and held in place by two wide head bolts which screw on to the nuts. Other applications of the string arrangement of the current invention are Corset, Boots, and many other fastening tools utilizing strings.

BRIEF DESCRIPTION OF THE DRAWINGS

FIG. 1 is a front view of a back supporting belt of prior art showing the arrangement of the fastening strings.

FIG. 1-a is a schematic diagram of the arrangement of strings of the prior art.

FIG. 2 is a front view of the back supporting belt of current invention showing the arrangement of the fastening strings.

FIG. 2-a is a schematic diagram of the arrangement of strings of the current application.

FIG. 3-a is a schematic drawings showing the back supporting belt worn by patient with a narrow upper stomach and a broad pelvis.

FIG. 3-b is a schematic diagram showing the back supporting belt worn by patient with a broad upper stomach and a narrow pelvis.

FIG. 4-a is a front view of the back supporting frame of the previous application looking from the out side of the frame when it is stretched.

FIG. 4-b is an expanded perspective view of the back supporting frame of the previous application from inside of the frame.

FIG. 6-a. is a perspective drawing of the frame of FIG. 4-a, when it is worn by a user having narrow upper stomach and a broad pelvis, fastened by pulling the right handle.

FIG. 6-b. is a perspective drawing of the frame of FIG. 4-a, when it is worn by a user having broad upper stomach and a narrow pelvis, fastened by pulling the left handle.

DETAILED DESCRIPTION OF THE PREFERRED EMBODIMENT

Figure 5:
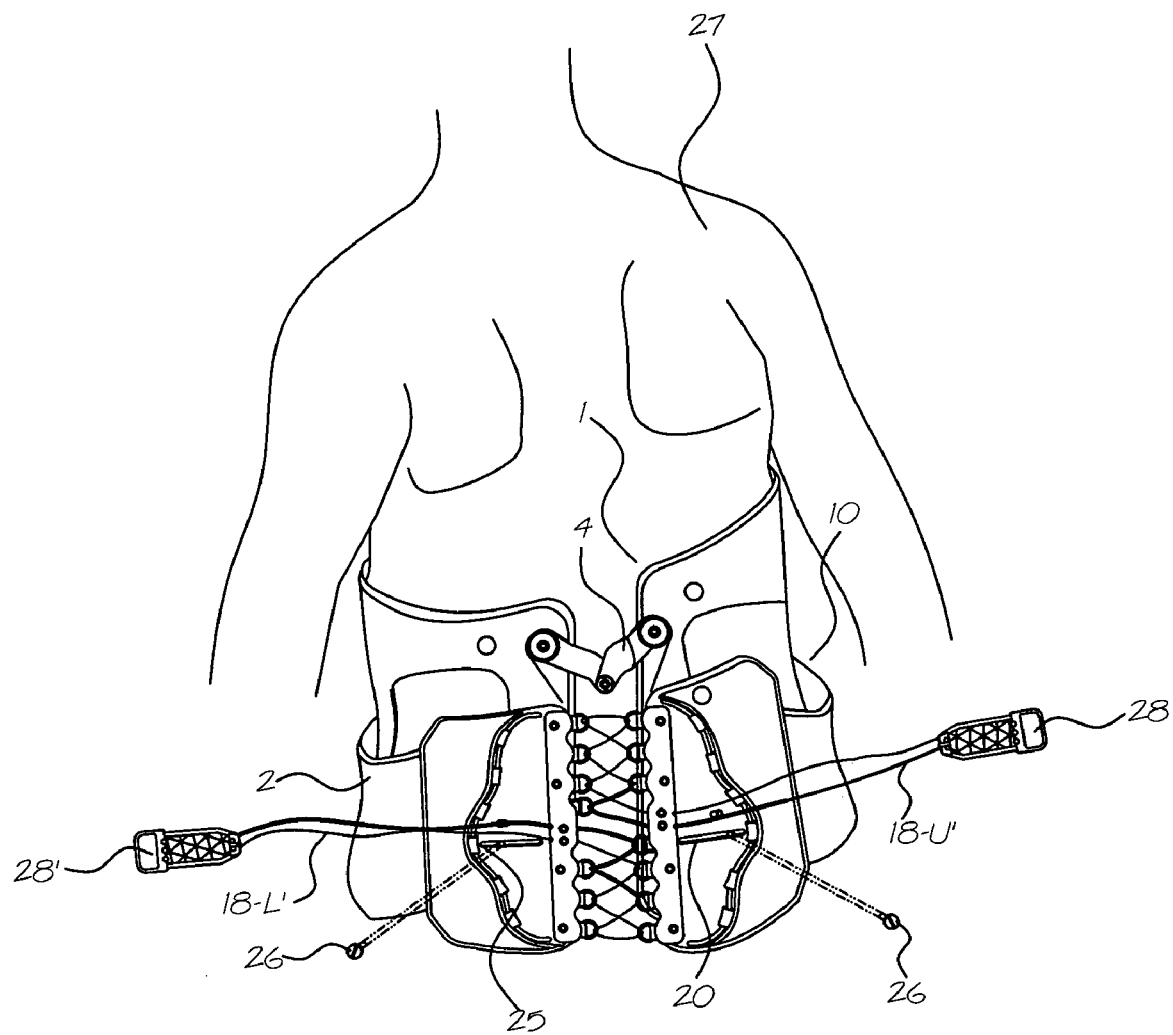
FIG. 5 is a schematic diagram showing how to attach the back support frame to the back supporting belt and how to put the back support frame on the patient's back.

FIG. 1 is a front view of a back supporting belt (10) of prior art showing the arrangement of the fastening strings. The belt (10) is comprised of, including but not limited, two bands (11) of equal width, which are comprised of, an elastic layer (12) and a plastic mesh (13) threaded together along the perimeters (14), and two fastening connectors (15), each of which are made of a solid plastic plate (16), equipped with eight triangular eyelets (17) for receiving the tightening strings (18) and a fabric fastener attached plastic mesh (19). Two narrow and long holes (20) are developed on the wider portion of each of the bands (11).

The outer layers of the bands (11) are made of plastic mesh (13) and fabric fastener. Fabric fastener's are found on both of the narrow ends of the outer surfaces (22) of the bands (11), on both of the wider ends of the outer surfaces (23) of the bands (11), and along the horizontal center (24) of the outer surfaces of the bands (11). The fastening connectors (15) are attached to the fabric fasteners on both of the wider ends of the outer surfaces (23) of the bands (11).

FIG. 1-a is a schematic diagram of the arrangement of the tightening strings (18) of the prior art. Upper-string (18-U) connects even number, 8 for example, of eyelets (17) on the upper part of the connectors (15) in zigzag pattern. Equal numbers of eyelets (17) are found on either inner perimeter of the upper-part of the fastening connectors (15). Lower-string (18-L) connects the eyelets (17) found on either inner perimeter of the lower part of the connectors by the same way. One end of the upper-string (18-U) and one end of the lower-string (18-L) are connected to a handle (28) of the fastening strings (18). The other ends of the upper- and lower-strings are connected to the other handle (28). If the wearer (27) pulls one of the handles (28), the distance (29) between the upper- and lower-part of the fastening connectors (15) decreases.

FIG. 2 is a front view of the back supporting belt (10) of the current invention showing the arrangement of the fastening strings. All the parts, except the arrangement of strings (18') and number of eyelets, pulleys or posts (17'), seven on each fastening connector (15), are the same as those of FIG. 1.

FIG. 2-a is a schematic diagram of the arrangement of strings (18') of the current application. Upper-string (18-U') connects odd numbers of eyelids (17') found on each upper part of the connectors (15) in a zigzag form. Both ends of the upper-string (18-U') are connected to a right string handle (28). Lower-string (18-L') also connects odd numbers of eyelids (17') found on each lower part of the connectors in the same manner. Both ends of the lower-string are connected to left string handle (28'). As a result, each connector is equipped with odd numbers of eyelids (17'). The shape of the arrangement of the upper part and lower part of the band is overlapped at 180 degree turn, but does not have mirror reflection image. Meanwhile, the shape of the arrangement of Chung's '529 has mirror reflection image. When a wearer (27) pulls the right string handle (28), an upper-string (18-U') is connected thereto, only the distance (29) between the upper parts of the connecting plates (15) is decreased. Similarly, if the wearer (27) pulls the left string handle (28'), only the distance (29) between the lower parts of the connectors (15) decreases. This difference in connection of both ends of a string to a string handle enables a separate fastening of the upper-part and lower-part of the belt.

One advantage of the above two pulling strings design incorporated with separate location of the upper and lower part of a fastening means can reduce the amount of pulling strength for tightening a selected portion, the wearer (patient) can compress the abdominal part more tightly with same force.

FIG. 3-a and FIG. 3-b are schematic drawings showing the back supporting belt worn by patients with varied waist contours. When a patient (27) fastens the upper-strings (18-U') by pulling the right handle (28) and leaves the left handle (28'), the upper parts of the wider portion of the two bands (11) comes closer. Then the bands (11) and connecting plates (15) create a configuration of belt (10) shown in FIG. 3-a, which fits the contour of the lower back of a wearer (27) with a narrow upper stomach and a broad pelvis.

By the same procedure, pulling the left handle (28') and leaving the right handle (28) creates a configuration of belt

(10) shown in FIG. 3-b which fits the contour of the lower back for a wearer (27) with a broad upper stomach and a narrow pelvis.

FIG. 4-a is a front view of the back supporting frame (1) of the previous application, U.S. patent application Ser. No. 10/810,860, looking from the outside of the frame when it is stretched. And FIG. 4-b is an expanded perspective view of the back supporting frame from inside of the frame. The supporting frame (1) is comprised of, including but not limited to, two plastic plates (2), each of which has a window (3) at the center and one guiding nut (25) on the center of the exterior side of the inner-half of the rim, connected by two hinges (4), which are attached to the upper and lower parts of the plastic plates, to form a saddle like shape that fits the contour of the waist of an individual patient.

Two sheets of plastic mesh (5) line the inside of each plastic plate (2). Two sheets of a soft elastic layer (6), with pluralities of holes (7) for air ventilation are threaded to the inside of each of the plastic mesh sheets, providing a cushion layer between the waist of the individual patient and the two plastic plates (2) attached to the frame (1). The perimeters (8) of the plastic mesh (5) and the elastic layer (6) are threaded to become one piece. The mesh (5) and the elastic layer (6) are attached to the back support plates (2) via snap buttons (9).

FIG. 5 is a schematic diagram showing how to attach the back support frame (1) to the back supporting belt (10) and how to put the back support frame (1) on the patient's back. The back supporting frame (1) is attached to the belt (10) via two guiding nuts (25), fixed on the center of the exterior side of the inner-half of the rim of each solid plastic plate (2), guided through the two narrow and long holes (20) found on the wider portions of the belt, and held in place by two wide head bolts (26) which screw on to the nuts. This diagram demonstrates how a patient (27) places the supporting frame (1) and belt (10) around the waist, joins the fabric fastener or open and closed loop (hook and loop closure) (21) and (24), and pulls the handles (28) of the fastening strings (18).

When a patient (27) fastens the upper-strings (18-U') by pulling the right handle (28) and leaves the left handle (28'), the upper parts of the wider portion of the two bands (11) comes closer and as a result squeeze the upper portion of the frame (1). Then the hinge (4-U) connecting the upper part of the two plates (2) folds and creates a configuration of frame (1) shown in FIG. 6-a, which fits the contour of the lower back of a wearer (27) with a narrow upper stomach and a broad pelvis.

By the same procedure, pulling the left handle (28') and leaving the right handle (28) creates a configuration of frame (1) shown in FIG. 6-b which fits the contour of the lower back for a wearer (27) with a broad upper stomach and a narrow pelvis. The limitations of a supporting plate comprised of one piece of plastic are overcome by the introduction of a flexible plastic and the utilization of the said string arrangement, enabling the creation of varied contour configurations as demonstrated previously.

The limitations of a supporting plate comprised of one piece of plastic are overcome by the introduction of a flexible plastic and the utilization of the said string arrangement, enabling the creation of varied contour configurations as demonstrated previously.

What is claimed is:

1. An arrangement of fastening strings for a detachment type waist protecting belt, which is comprised of two bands of equal width, which are comprised of, an elastic layer and a plastic mesh threaded together along the perimeters, and left and right fastening connectors, each of which are made of a solid plastic plate, equipped with odd numbers of triangular eyelets, four eyelids on a upper part and three eyelids on a lower part of the left connector and three eyelids on the upper part and four eyelids on lower part of right connector, for receiving two identical strings, a left string handle that is connected to both ends of one of the fastening string which is engaged to the lower-part of the fastening connectors in zigzag pattern, a right string handle that is connected to both ends of the other fastening string that is engaged to the upper-part of the fastening connectors in zigzag pattern, and a fabric fastener attached plastic mesh, to hold the vertebra region of a vertebra related patient enabling a separate fastening of the upper-part and lower-part of the belt to form a saddle like shape that fits the contour of the waist of an individual patient dynamically and permits separate inferior and superior pressure to be applied to the rib and upper stomach and the pelvis region of a patient.

2. An arrangement of fastening string in claim 1, wherein both ends of the upper-part fastening string are connected to the right fastening handle after one end of the upper-part fastening string passes through, in zigzag pattern, odd numbers of eyelids attached on both of the upper-parts of the two fastening connectors.

3. The number of eyelids in claim 2, wherein the number of the eyelids on the upper-part of the left fastening connectors is one greater than that of the eyelids in the upper-part of the right fastening connector.

4. An arrangement of fastening string in claim 1, wherein both ends of the lower-part fastening string are connected to the left fastening handle after one end of the lower-part fastening string pass through every odd numbers of eyelids, in zigzag pattern, attached on both of the lower-parts of the fastening connectors.

5. The number of eyelids in claim 4, wherein the number of the eyelids in lower part of the right fastening connector is one greater than that of the eyelids in the lower part of the left fastening connector.

* * * * *